US00PP18129P3

(12) United States Plant Patent
Muranaka et al.

(10) Patent No.: US PP18,129 P3
(45) Date of Patent: Oct. 16, 2007

(54) VARIETY OF JAPANESE BLACK PINE NAMED KANEMI

(50) Latin Name: *Pinus thumbergiana*
Varietal Denomination: Kanemi

(76) Inventors: Kanemi Muranaka, 417 Pajaro La., Nipomo, CA (US) 93444; George Muranaka, 419 Pajaro La., Nipomo, CA (US) 93444

( * ) Notice: Subject to any disclaimer, the term of this patent is extended or adjusted under 35 U.S.C. 154(b) by 0 days.

(21) Appl. No.: 11/332,552

(22) Filed: Jan. 12, 2006

(65) Prior Publication Data

US 2007/0163019 P1 Jul. 12, 2007

(51) Int. Cl.
*A01H 5/00* (2006.01)

(52) U.S. Cl. ..... Plt./213

(58) Field of Classification Search ..... Plt./213
See application file for complete search history.

*Primary Examiner*—Kent Bell
*Assistant Examiner*—Annette H Para
(74) *Attorney, Agent, or Firm*—Kauth, Pomeroy, Peck & Bailey LLP

(57) ABSTRACT

A new and distinct variety of *Pinus thumbergiana* named 'Kanemi', being distinctively different, smaller in size and with shorter needles, than known *Pinus thumbergiana* cultivars.

3 Drawing Sheets

Classification: The present invention relates to a new *Pinus thumbergiana* plant.

Variety denomination: The new plant has the varietal denomination 'Kanemi'.

BACKGROUND

This invention relates to a new and distinct variety of *P. thumbergiana* plant named 'Kanemi', discovered as a sport in a controlled planting of Japanese Black Pine in Nipomo, Calif. The sport parent is unknown. The new variety was discovered in approximately 2001 in a planted row of Japanese Black Pine, all of the same age, when it was observed that one of the plants was distinctively different, smaller in size and with shorter needles.

SUMMARY OF THE INVENTION

Among the features which distinguish the new variety from other presently available and commercial Japanese Black Pine cultivars known to the inventor are the following combination of characteristics:

1. Smaller size than same-aged members of other Japanese Black Pine cultivars; after 1–2 years growth, plants of the new variety have an average height of approximately 70 cm while other Japanese Black Pine cultivars of the same age have an average height of approximately 142 cm to 213 cm.
2. Smaller trunk diameter, with 1- to 2-year old plants of the new variety having an average trunk diameter of approximately 1.6 cm while other Japanese Black Pine cultivars of the same age have an average trunk diameter of approximately 3.5 cm to 5.7 cm.
3. Shorter needle length, with 1- to 2-year old plants of the new variety having an average needle length of approximately 12.5 mm to 25 mm, while other Japanese Black Pine cultivars of the same age have an average needle length of approximately 10 cm to 15.2 cm.

Asexual reproduction of the new variety 'Kanemi' by grafting on a regular Japanese Black Pine *P. thumbergiana* rootstock was performed in Nipomo, Calif., and shows that the foregoing and other distinguishing characteristics come true to form and are established and transmitted through succeeding asexual propagations.

DETAILED DESCRIPTION OF THE INVENTION

The following detailed description of the new variety is based upon observations taken of ten year old plants grown outdoors in fields in Nipomo, Calif., with a range of day temperatures from 60° to 85° F., and a range of night temperatures from 30° to 55° F.

The following description is in accordance with UPOV terminology and the color terminology herein is in accordance with The Royal Horticultural Society Colour Chart (R.H.S.). The color descriptions and other phenotypical descriptions may deviate from the stated values and descriptions depending upon variation in environmental, seasonal, climatic and cultural conditions.

Figure 1:
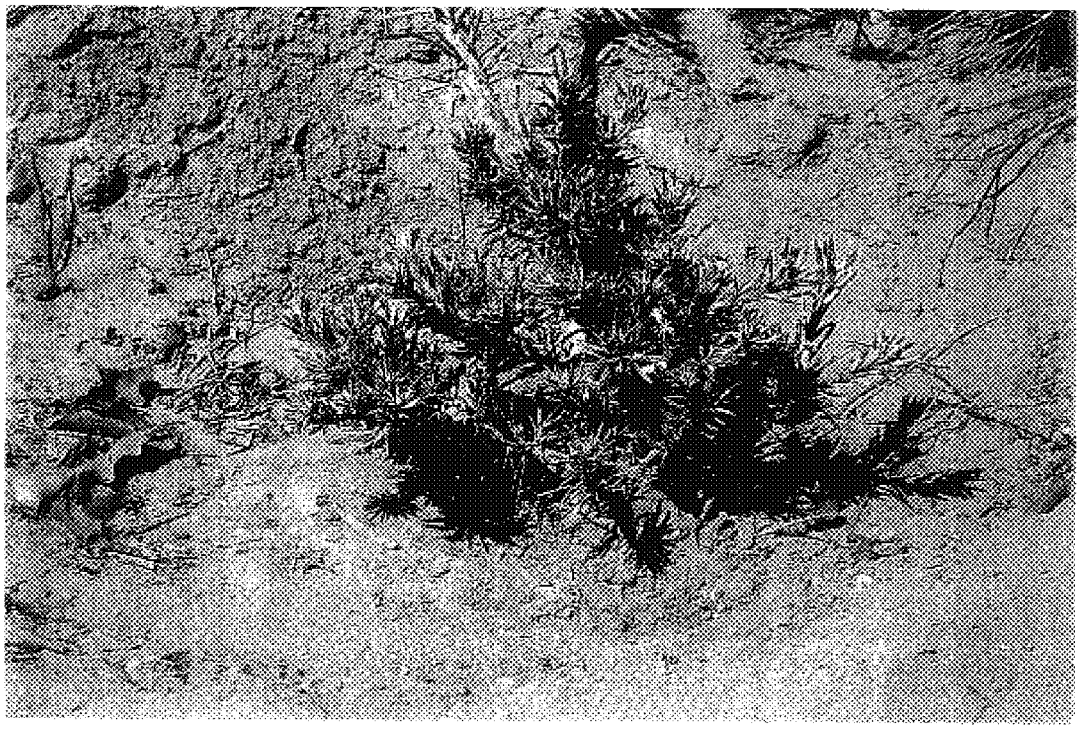
FIG. 1 shows a close-up of the new variety.
Figure 2:
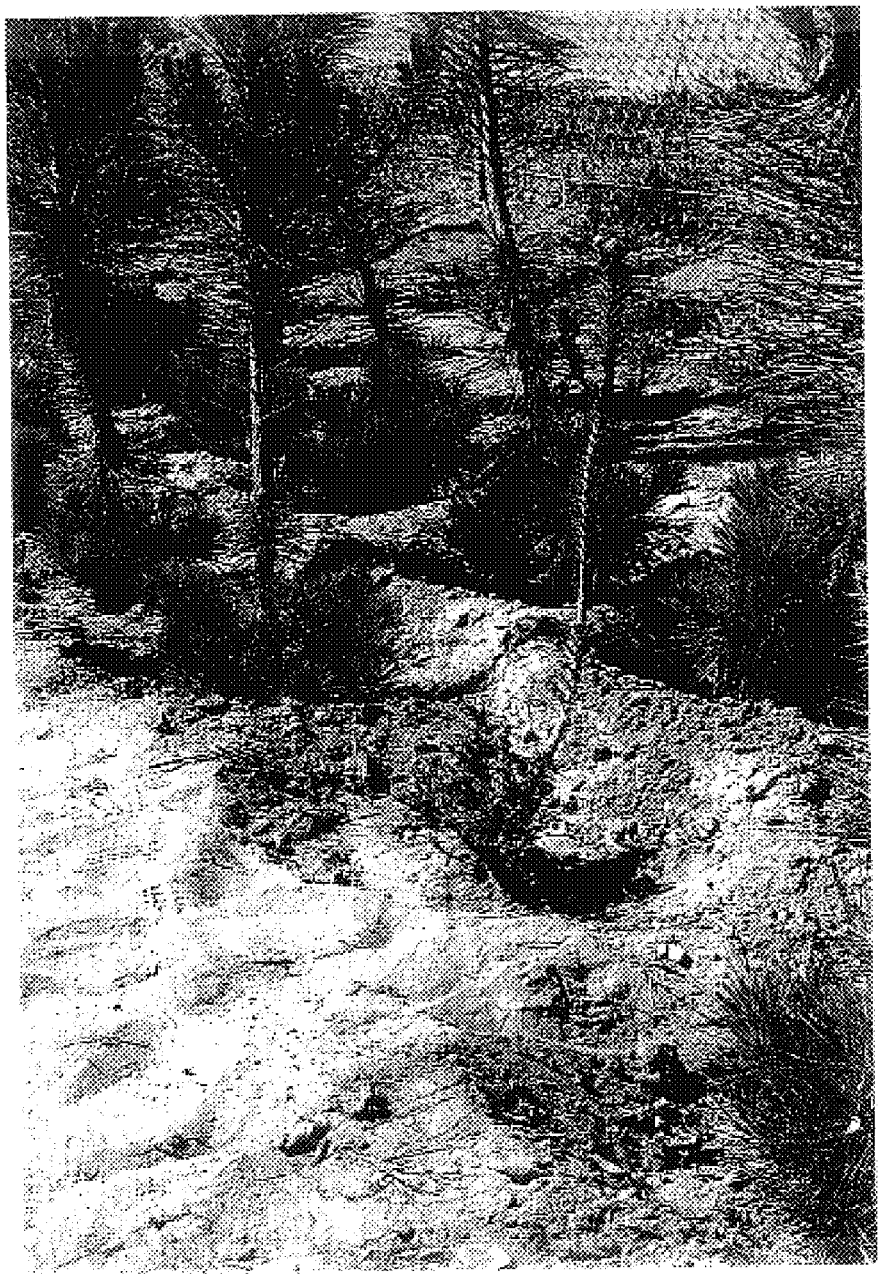
FIG. 2 shows the new variety growing along side commercially-available Japanese Black Pine cultivars of the same age.

Plant:

*Shape.*—Normal shape of the new variety is pyramidal, but is typically pruned to become a bonsai. The tree has a long leader at top and all branching is low, as shown in FIGS. 1 and 2.

*Height.*—About 70 cm.

*Diameter.*—About 22 cm.

*Growth rate.*—Slower than found in other Japanese Black Pine varieties.

Roots:

*Time to initiate.*—About 2 to 4 weeks.

*Form.*—Roots start out fine, becoming larger as plant grows. New fine roots develop from older roots.

Trunk:

*Diameter.*—Trunk is about 18 mm at 25 mm from soil level narrowing to 10 mm at 30 cm from soil level.

*Texture.*—Rough, slightly raised bark structure.

*Color.*—Greyed-green varying around Group 188B–D.

Branches:

*Habit.*—Branches grow approximately 3 to 4 cm, then new branch shoots form, radiating from the older branch.

*Number.*—Typically 10 lateral branches are observed (some are pruned to provide the bonsai shape).

*Length.*—About 6 to 12 cm.

*Diameter.*—About 4 to 5 mm.

*Internode length.*—About 3 to 4 cm.

*Color.*—Greyed-green varying around Group 188B–D.

Figure 3:
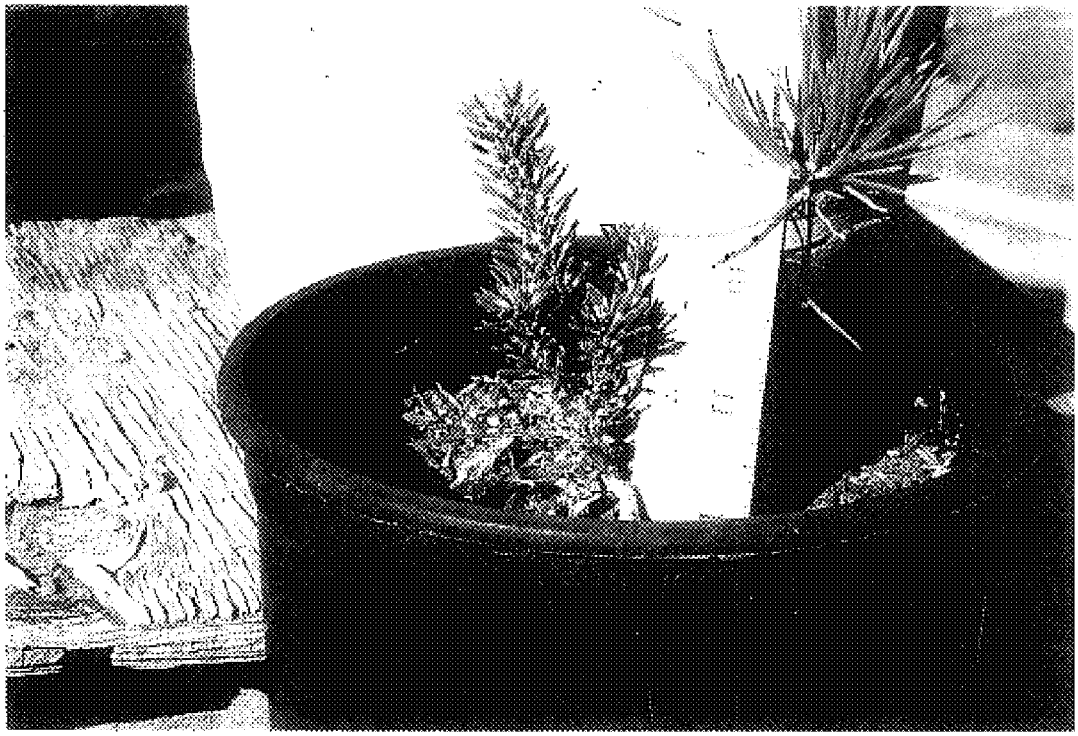
FIG. 3 shows the new variety grafted onto a commercially-available Japanese Black Pine cultivar, illustrating the difference in needle-length.

Foliage:

*Needle arrangement.*—Two needles per sheath, as shown in FIG. 3.

*Size.*—Needle length varies from about 1 cm in new growth to about 2 cm for needles aged one year or older.

Cones: Cones form, but seeds have not yet been collected.

*Dimensions.*—Unopened cone is 20 mm long and 15 mm in diameter.

*Shape.*—Ovoidal.

*Color.*—Greyed-orange varying around Group 164C-D.

I claim:

1. A new and distinct variety of *Pinus thumbergiana* tree, identified as 'Kanemi', substantially as shown and described.

* * * * *